(12) United States Patent
Enoki et al.

(10) Patent No.: US 11,197,614 B2
(45) Date of Patent: Dec. 14, 2021

(54) BIOLOGICAL MATERIAL MEASURING APPARATUS AND METHOD OF MEASURING BIOLOGICAL MATERIAL

(71) Applicant: Mitsubishi Electric Corporation, Chiyoda-ku (JP)

(72) Inventors: Kentaro Enoki, Chiyoda-ku (JP); Kosuke Shinohara, Chiyoda-ku (JP); Koichi Akiyama, Chiyoda-ku (JP); Shimpei Ogawa, Chiyoda-ku (JP); Daisuke Fujisawa, Chiyoda-ku (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 233 days.

(21) Appl. No.: 16/344,615

(22) PCT Filed: Sep. 22, 2017

(86) PCT No.: PCT/JP2017/034319
§ 371 (c)(1),
(2) Date: Apr. 24, 2019

(87) PCT Pub. No.: WO2018/123169
PCT Pub. Date: Jul. 5, 2018

(65) Prior Publication Data
US 2020/0060549 A1    Feb. 27, 2020

(30) Foreign Application Priority Data

Dec. 26, 2016   (JP) .............................. JP2016-251325

(51) Int. Cl.
*G01N 21/25*   (2006.01)
*A61B 5/00*    (2006.01)
(Continued)

(52) U.S. Cl.
CPC .......... *A61B 5/0075* (2013.01); *A61B 5/1477* (2013.01); *G01J 3/14* (2013.01); *G01J 3/42* (2013.01); *G01J 2003/425* (2013.01)

(58) Field of Classification Search
CPC ...... G01J 3/51; G01J 3/513; G01J 3/50; G01J 3/46; G01J 3/02
(Continued)

(56) References Cited

U.S. PATENT DOCUMENTS

2006/0164633 A1* 7/2006 Koshoubu ................ G01J 3/02
                                                       356/300
2009/0122317 A1   5/2009 Ito et al.
(Continued)

FOREIGN PATENT DOCUMENTS

CN       106102579 A    11/2016
JP       60-75031 A      4/1985
(Continued)

OTHER PUBLICATIONS

International Search Report dated Dec. 12, 2017, in PCT/JP2017/034319 filed on Sep. 22, 2017.
(Continued)

*Primary Examiner* — Md M Rahman
(74) *Attorney, Agent, or Firm* — Xsensus LLP

(57) ABSTRACT

An infrared light source radiates, to an ATR prism, infrared light in entirety or part of a wavelength range with absorption wavelengths of a biological material. The ATR prism is adherable to a measurement skin. A prism vibration controller is mounted on the ATR prism and vibrates the ATR prism perpendicular to a contact surface between the ATR prism and the measurement skin. A controller causes an infrared photodetector to detect infrared light in synchronization with the vibration of the ATR prism.

17 Claims, 9 Drawing Sheets

(51) Int. Cl.
   *A61B 5/1477*   (2006.01)
   *G01J 3/14*     (2006.01)
   *G01J 3/42*     (2006.01)

(58) Field of Classification Search
   USPC ........................................................ 356/406
   See application file for complete search history.

(56) References Cited

U.S. PATENT DOCUMENTS

| | | | |
|---|---|---|---|
| 2015/0185207 A1* | 7/2015 | Black ................... | A61B 5/6826 |
| | | | 435/29 |
| 2016/0143539 A1* | 5/2016 | Koerner ............... | A61B 5/4836 |
| | | | 600/427 |

FOREIGN PATENT DOCUMENTS

| JP | 2-140639 A | 5/1990 |
| JP | 2003-35661 A | 2/2003 |
| JP | 2003-42952 A | 2/2003 |
| JP | 2005-188999 A | 7/2005 |
| JP | WO 2007/034681 A1 | 3/2007 |
| JP | 2012-191969 A | 10/2012 |
| WO | 2015/167417 A1 | 11/2015 |

OTHER PUBLICATIONS

Office Action dated May 10, 2021 in Chinese Patent Application No. 201780078201.5, 21 pages.
German Office Action dated Aug. 12, 2021 in German Application No. 11 2017 006 536.4.

* cited by examiner

BIOLOGICAL MATERIAL MEASURING APPARATUS AND METHOD OF MEASURING BIOLOGICAL MATERIAL

TECHNICAL FIELD

The present invention relates to biological material measuring apparatuses and methods of measuring biological material, and more particularly, to a biological material measuring apparatus and a method of measuring a biological material for measuring a biological material such as sugar in a living body using infrared light.

BACKGROUND ART

A conventional invasive sensor draws blood with a needle and analyzes a component of a material in a living body. In particular, for blood sugar level sensors commonly used, a non-invasive type is desired to alleviate patient's pain caused by puncture. Although one type of non-invasive blood sugar level sensor using infrared light is capable of directly detecting a fingerprint spectrum of sugar, infrared light cannot reach a deep portion from a skin surface because infrared light is absorbed well by water. Under the circumstances, such a technique is demanded that detects a blood sugar level stably with high accuracy even when absorption by sugar in a living body is little.

In response to such a demand, for example, the apparatus described in PTL 1 has an SN ratio improved through a measurement using an attenuated total reflection (ATR) prism. The infrared light propagating through the ATR prism repeats reflection at an interface between a measurement skin and the ATR prism. Evanescent light is generated at the interface at which reflection occurs, and then penetrates the measurement skin. Since the evanescent light is absorbed and scattered by water, sugar, and any other biological material, the intensity of the infrared light propagating through the ATR prism attenuates. Thus, the intensity of propagating infrared light attenuates more with a larger number of repetitions of reflection. According to this literature, a semiconductor quantum cascade can be used as an infrared light source to miniaturize the infrared light source to be mounted in a mobile telephone.

PTL 2 describes an apparatus that changes a pressure applied to a measurement object, which is disposed between a prism and an actuator, and measures an infrared absorption spectrum.

CITATION LIST

Patent Literature

PTL 1: Japanese Patent Laying-Open No. 2003-42952
PTL 2: Japanese Patent Laying-Open No. 2003-35661

SUMMARY OF INVENTION

Technical Problem

A skin is composed of an epidermis near a skin surface and a corium below the epidermis. The epidermis includes a stratum corneum, a stratum granulosum, a stratum spinosum, and a stratum basale in order from the vicinity of the skin surface. Sugar and any other biological material, which are present in an interstitial fluid of the epidermis, are conceivably distributed nonuniformly in the depth direction while reflecting the structure of the epidermis.

When the epidermis receives a stress due to a contact between the ATR prism and the skin surface, the structure of the epidermis becomes distorted. Since a change in the contact state between the ATR prism and the skin surface changes the contact stress which the skin surface receives from the ATR prism, the distribution of the interstitial fluid in the epidermis also changes. This may lead to variations in the intensity of the evanescent light of infrared light which is absorbed by sugar and any other biological material.

According to PTL 2, a pressure is periodically applied to a measurement material with the measurement material adhering to a prism, and a modulating signal is extracted in response to a pressure change. If a living body is a measurement object, however, it is difficult to periodically change the pressure on the measurement material side.

An object of the present invention is therefore to provide a biological material measuring apparatus and a method of measuring a biological material that can prevent degradation of an accuracy with which an amount of a biological material in a measurement skin is measured, depending on a contact state between an ATR prism and the measurement skin.

Solution to Problem

In order to solve the above problem, a biological material measuring apparatus of the present invention includes an ATR prism, an infrared light source, an infrared photodetector, a prism vibration controller, and a controller. The ATR prism is adherable to a measurement skin. The infrared light source is configured to radiate, to the ATR prism, infrared light in entirety or part of a wavelength region with absorption wavelengths of a biological material. The infrared photodetector is configured to detect infrared light emitted from the ATR prism. The prism vibration controller is mounted on the ATR prism and configured to vibrate the ATR prism perpendicular to a contact surface between the ATR prism and the measurement skin. The controller is configured to cause the infrared photodetector to detect the infrared light in synchronization with the vibration.

Advantageous Effects of Invention

According to the present invention, the ATR prism is caused to vibrate perpendicular to the contact surface between the ATR prism and the measurement skin, and infrared light is detected in synchronization with the vibration, thereby preventing degradation of an accuracy with which an amount of a biological material in a measurement skin is measured, depending on the contact state between the ATR prism and the measurement skin.

DESCRIPTION OF EMBODIMENTS

Embodiments of the present invention will now be described with reference to the drawings.

Embodiment 1

Although description will be given below by taking a blood sugar level as an example measuring object, a measuring apparatus of the present invention is applicable to measurement of a blood sugar level, as well as measurement of any other biological material.

Figure 1:
FIG. 1 shows an example use of mobile non-invasive blood sugar level sensors 80 of Embodiments 1 to 5.

FIG. 1 shows an example use of mobile non-invasive blood sugar level sensors 80 according to Embodiments 1 to 5.

As shown in FIG. 1, the blood sugar level of a living body of a subject is measured while bringing the head of mobile non-invasive blood sugar level sensor 80 into contact with a subject's lip with a thin keratin layer. Although a measurement site is desirably a lip with a thin keratin layer, it may be another site. It suffices that the measurement site is other than a site with a thick keratin layer, such as a palm. For example, measurements can also be made on a cheek of a face, an earlobe, or the back of a hand.

Figure 2:
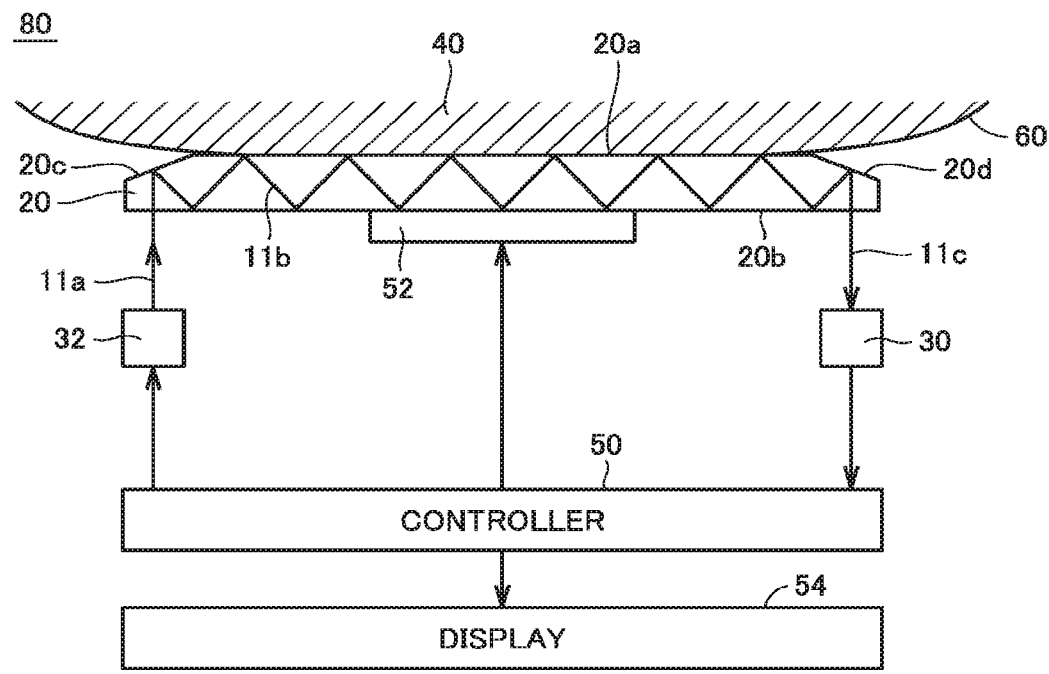
FIG. 2 shows a configuration of mobile non-invasive blood sugar level sensor 80 of Embodiment 1.
Figure 3:
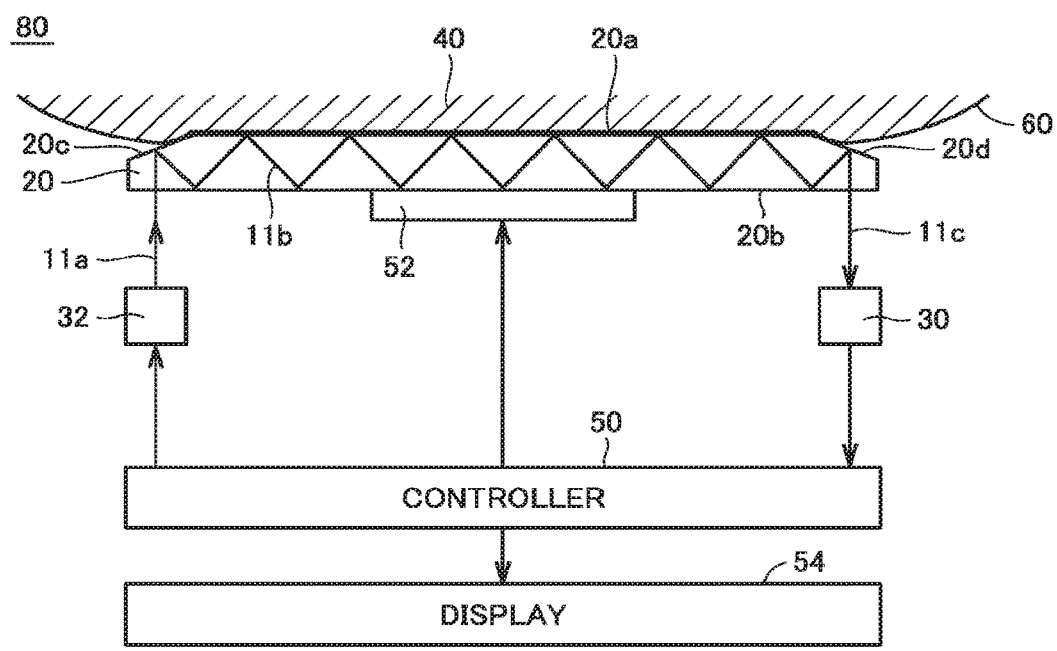
FIG. 3 shows a configuration of mobile non-invasive blood sugar level sensor 80 of Embodiment 1.

FIGS. 2 and 3 show a configuration of mobile non-invasive blood sugar level sensor 80 of Embodiment 1. The contact state between non-invasive blood sugar level sensor 80 and a measurement skin 40 differs between FIGS. 2 and 3.

As shown in FIGS. 2 and 3, non-invasive blood sugar level sensor 80 includes an ATR prism 20, a prism vibration controller 52, an infrared light source 32, an infrared photodetector 30, a controller 50, and a display 54.

Infrared light source 32 radiates, to ATR prism 20, infrared light in entirety or part of a wavelength range with absorption wavelengths of a biological material.

Infrared photodetector 30 detects infrared light emitted from ATR prism 20. Herein, a value to be detected may be the intensity (power) of light with a certain wavelength or a light spectrum. Description will be given below assuming that the intensity at a certain wavelength is detected.

Controller 50 controls prism vibration controller 52, infrared light source 32, and infrared photodetector 30. Controller 52 detects the concentration of the blood sugar level of a living body based on the intensity of the infrared light detected by infrared photodetector 30.

ATR prism 20 is mounted on the head of non-invasive blood sugar level sensor 80. ATR prism 20 is in contact with a skin surface 60 of measurement skin 40.

Figure 4:
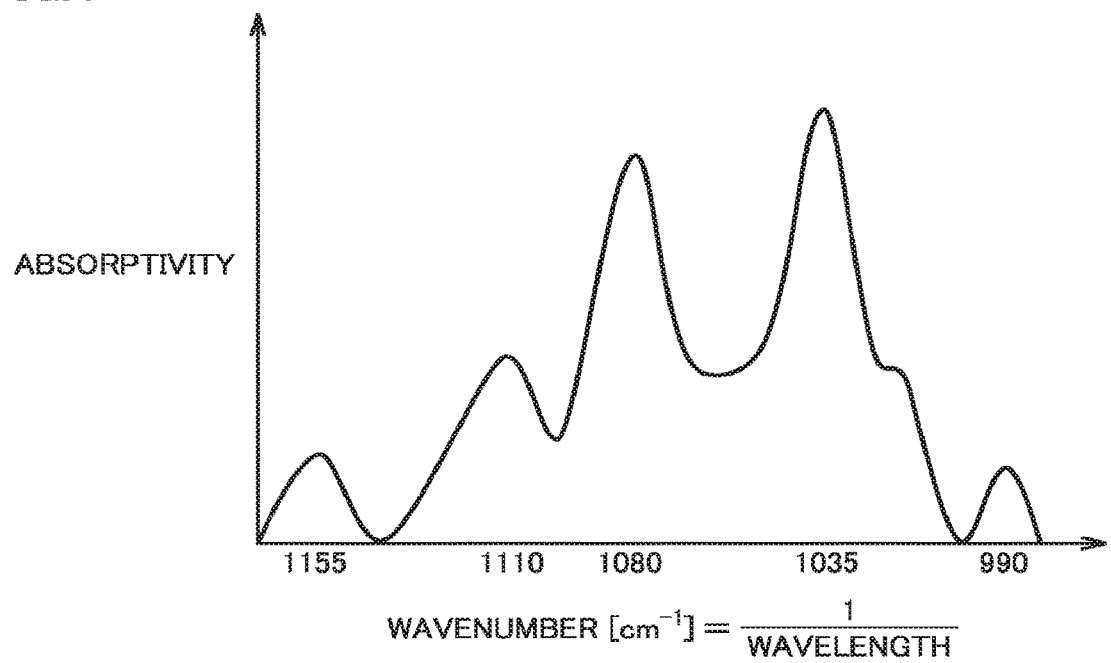
FIG. 4 shows a fingerprint spectrum of sugar.

FIG. 4 shows a fingerprint spectrum of sugar.

When non-invasive blood sugar level sensor 80 is activated with ATR prism 20 brought into contact with skin surface 60 of the subject, infrared light source 32 radiates infrared light in entirety or part of the wavelength region in the wavelength range of 8.5 µm to 10 µm, which includes a fingerprint spectrum of sugar. Incoming infrared light 11a emitted from infrared light source 32 is reflected off an end face 20c of ATR prism 20 and then turns into propagating infrared light 11b. Propagating infrared light 11b passes through ATR prism 20 being in contact with measurement skin 40 while repeating reflection off end faces 20a and 20b of ATR prism 20. Propagating infrared light 11b that has passed through ATR prism 20 is reflected off an end face 20d of ATR prism 20 and then turns into radiated infrared light 11c. Infrared photodetector 30 detects the intensity of radiated infrared light 11c.

Evanescent light is generated at the interface (end face 20a) between ATR prism 20 and measurement skin 40. This evanescent light penetrates measurement skin 40 and is absorbed by sugar.

A smaller difference in the refractive index between measurement skin 40 and ATR prism 20 results in more intense evanescent light. The evanescent light which has leaked from ATR prism 20 toward measurement skin 40 in reflection at the interface (end face 20a) is absorbed by the biological material in measurement skin 40, so that the intensity of the infrared light reflected off end face 20a attenuates. A larger amount of biological material accordingly leads to more absorption of evanescent light, resulting in more attenuation of the intensity of the infrared light subjected to reflection.

A skin is composed of an epidermis near a skin surface and a corium below the epidermis. The epidermis includes a stratum corneum, a stratum granulosum, a stratum spinosum, and a stratum basale in order from the vicinity of the skin surface, the thicknesses of which are about 10 µm, about several micrometers, about 100 µm, and about several micrometers, respectively. Cells are produced in the stratum basale and stacked on the stratum spinosum. Since water (interstitial fluid) does not reach the stratum granulosum, the cells die out. The dead cells are hardened in the stratum corneum. Sugar and any other biological material are present in the interstitial fluid of the epidermis. The interstitial fluid increases from the stratum corneum to the stratum spinosum. The intensity of the infrared light subjected to reflection accordingly changes in accordance with the penetration length of evanescent light. Herein, the penetration length is also referred to as a penetration depth.

Evanescent light attenuates exponentially from the interface toward measurement skin 40, and has a penetration length approximately equal to its wavelength. Spectroscopy using ATR prism 20 can thus measure an amount of a biological material in the region up to the penetration length. For example, a fingerprint spectrum of sugar has wavelengths of 8.5 µm to 10 µm, and accordingly, an amount of sugar in the region of about 8.5 µm to 10 µm from the prism surface of ATR prism 20 can be detected.

ATR prism 20 has a shape of a rectangular parallelepiped with missing parts. The cross-section of the ATR prism has a shape obtained by cutting two vertical angles from a rectangle at a certain angle. A shorter surface on which vertical angles are cut is brought into contact with measurement skin 40 as a measuring surface. The angle of end face 20c of ATR prism 20 is set such that propagating infrared light 11b in ATR prism 20 is reflected off end faces 20a and 20b of ATR prism 20. The angle of end face 20d of ATR prism 20 is set such that radiated infrared light 11c travels toward infrared photodetector 30. For example, the angle of end face 20d of ATR prism 20 is set such that radiated infrared light 11c perpendicularly enters infrared photodetector 30.

Infrared light source 32 and ATR prism 20 are disposed to keep a constant angle of incidence at which infrared light enters ATR prism 20 from infrared light source 32. Antireflection coating is applied to end face 20c on which incoming infrared light 11a from infrared light source 32 is incident and end face 20d from which radiated infrared light 11c exits toward infrared photodetector 30. Alternatively, incoming infrared light 11a from infrared light source 32 may be made p-polarized light, and incidence surface 20c and emission surface 20d may be chipped to make an angle of incidence/emission a Brewster's angle.

Used as the material for ATR prism 20 is a single crystal of zinc sulfide (ZnS) which is transparent in a mid-infrared range and has a relatively low refractive index. The material for ATR prism 20 is not limited to a single crystal of zinc sulfide (ZnS) and may be a known material such as zinc selenide (ZnSe). Contact surface 20a of ATR prism 20 which comes into contact with measurement skin 40 is coated with a thin film of, for example, $SiO_2$ or SiN to cause no harm to a human body.

Used as infrared light source 32 is, for example, a wide-band quantum cascade laser module. A quantum cascade laser, which includes a single light source and has a high output and a high signal-to-noise ratio (SN ratio), is capable of high-accuracy measurements. A lens for collimating a beam is mounted in the quantum cascade laser module. The wide-band quantum cascade laser radiates infrared light in entirety or part of the wavelength region in the wavelength range of 8.5 μm to 10 μm.

In addition to a wide-band quantum cascade laser, infrared light source 32 may be a thermal light source of the type that flows current through a filament for heating. In this case, temperature can be controlled by an amount of a current applied, and accordingly, wide-band infrared rays according to black body radiation are radiated. Alternatively, infrared light source 32 may not be a filament and may be a plasmon or a metamaterial light source that has a periodic pattern provided in a heating portion. In this case, infrared light source 32 is a high-efficiency light source because the radiation wavelength range is defined by surface structure and accordingly has reduced unnecessary radiation.

Radiated infrared light 11c radiated from ATR prism 20 is received by infrared photodetector 30. Infrared photodetector 30 detects outgoing light radiated from ATR prism 20. The value detected herein may be a light spectrum or power with a certain wavelength. Infrared photodetector 30 may include an array of non-cooling infrared sensors each detecting light with a different wavelength. The non-cooling infrared sensor may be a wavelength-selective absorber using a plasmon resonance on the surface of a light receiving portion. The non-cooling infrared sensor (thermal infrared sensor) may be a pyroelectric sensor or a sensor including a bolometer, thermopile, or a silicon on insulator (SOT) diode.

Depending on the contact state between ATR prism 20 and skin surface 60 of the subject, the structure of measurement skin 40 may distort, or the thickness of the water, oils and fats, or the like between ATR prism 20 and skin surface 60 may change, which changes a portion at which evanescent light arrives. For example, depending on the force by which ATR prism 20 is pressed, the thickness of a stratum corneum increases or decreases, which may or may not allow evanescent light to reach a stratum granulosum or a stratum spinosum.

Considering the above, prism vibration controller 52 is used to vibrate ATR prism 20 in the present embodiment. Infrared light is radiated from infrared light source 32 while vibrating ATR prism 20, and the infrared light is detected by infrared photodetector 30. At this time, prism vibration controller 52 and infrared photodetector 30 are synchronously controlled by controller 50.

Prism vibration controller 52 is mounted on ATR prism 20 and causes ATR prism 20 to vibrate perpendicular to skin surface 60 that is the contact surface between ATR prism 20 and measurement skin 40. For example, prism vibration controller 52 displaces or expands or contracts in response to a signal from controller 50 to vibrate ATR prism 20. Prism vibration controller 52 may be formed of, for example, a piezoelectric actuator or the like. Controller 50 causes infrared photodetector 30 to detect infrared light in synchronization with the vibration of ATR prism 20.

FIG. 3 shows a state in which ATR prism 20 is pressed against skin surface 60 by prism vibration controller 52 vibrating ATR prism 20.

Although ATR prism 20 is in contact with skin surface 60 in the state of any of FIGS. 2 and 3, an extent to which ATR prism 20 is pressed against skin surface 60 differs between the states of FIGS. 2 and 3.

As shown in FIG. 2, ATR prism 20 is in contact with skin surface 60 during one period of vibration of ATR prism 20. Herein, a weak adhesion state refers to a state in which during one period of vibration of ATR prism 20, ATR prism 20 is not pressed toward measurement skin 40, and the lowest stress acts on skin surface 60 that is the contact surface between ATR prism 20 and measurement skin 40.

A strong adhesion state refers to a state in which during one period of vibration of ATR prism 20, ATR prism 20 is pressed most deeply toward measurement skin 40, and the highest pressure acts on skin surface 60 that is the contact state between ATR prism 20 and measurement skin 40, as shown in FIG. 3.

Prism vibration controller 52 causes ATR prism 20 to repeat the vibration operation in which a state transition from the weak adhesion state of FIG. 3 to the strong adhesion state of FIG. 4 to the weak adhesion state of FIG. 3 is one period. Herein, it suffices that the amplitude of vibration, that is, a difference in the press distance between the weak adhesion state and the strong adhesion state is not more than several millimeters.

Infrared photodetector 30 detects radiated infrared light 11c radiated from ATR prism 20 in synchronization with the operation of prism vibration controller 52. Normally, radiated infrared light 11c detected by infrared photodetector 30 contains a spectral signal and electrical noise signals of the surroundings and a detector per se. Further, any gap between ATR prism 20 and skin surface 60 of the subject which are in contact with each other can cause noise, deteriorating a signal-noise ratio S/N of the detected value and reducing the penetration length of evanescent light.

Thus, infrared photodetector 30 detects radiated infrared light 11c several times at equal intervals during one period of vibration. In the present embodiment, infrared photodetector 30 detects radiated infrared light 11c twice at equal intervals during one period. Herein, two detection timings include a timing at which the weak adhesion state of FIG. 2 is provided and a timing at which the strong adhesion state of FIG. 3 is provided in order to obtain high detection sensitivity.

Then, controller 50 calculates a difference dS(=S(a)−S(b)), where S(a) is the intensity of radiated infrared light 11c detected by infrared photodetector 30 in the weak adhesion state of FIG. 2, and S(b) is the intensity of radiated infrared light 11c detected by infrared photodetector 30 in the strong adhesion state of FIG. 3. Controller 50 determines a plurality of dS's through a plurality of measurements and calculates a sum ΣdS thereof.

Figure 5:
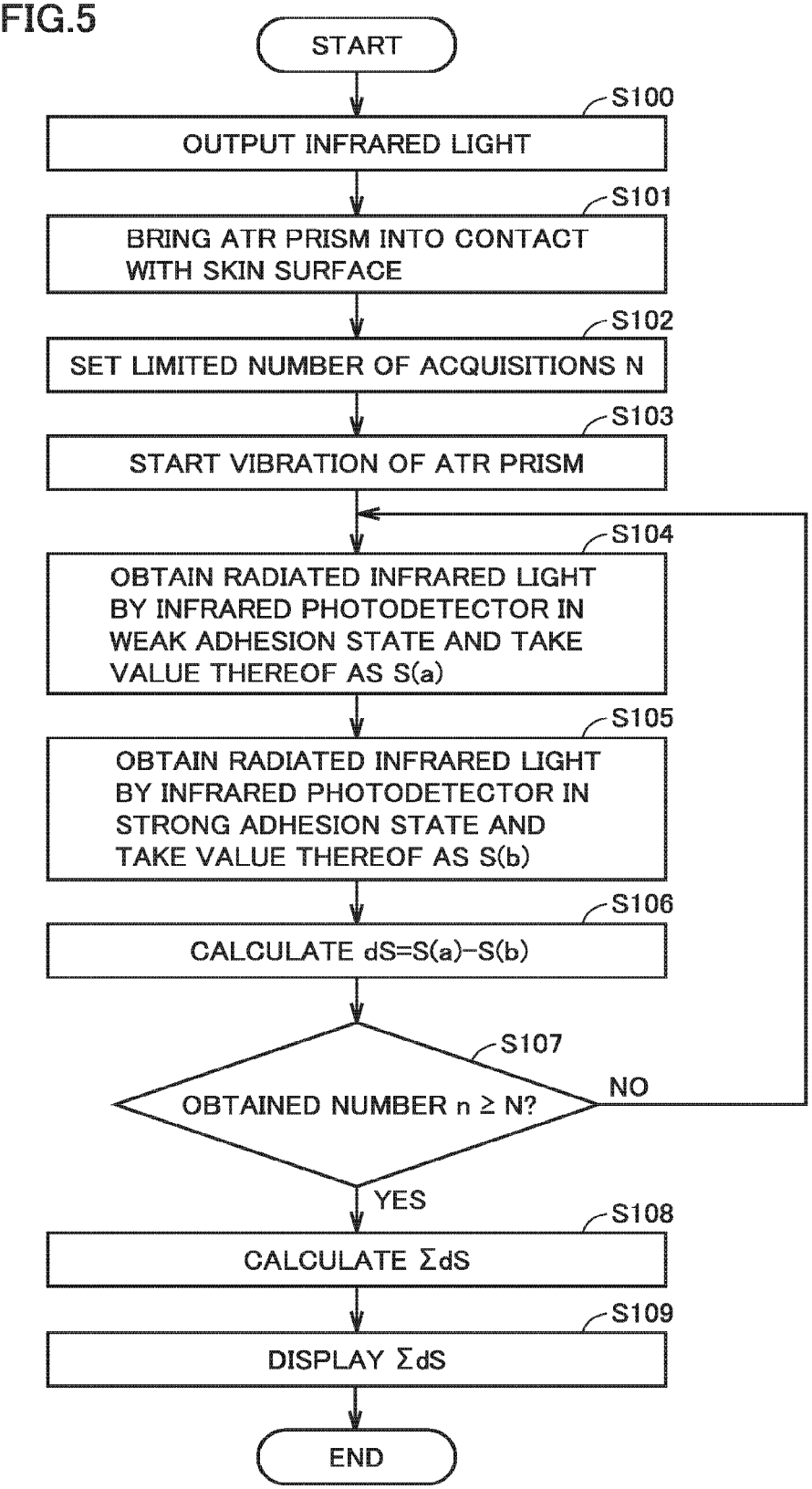
FIG. 5 is a flowchart showing an operational procedure of mobile blood sugar level sensor 80 of Embodiment 1.

FIG. 5 is a flowchart showing an operational procedure of blood sugar level sensor 80 in Embodiment 1.

At step S100, infrared light source 32 outputs infrared light.

At step S101, ATR prism 20 is brought into contact with skin surface 60 of the subject.

At step S102, controller 50 sets a limited number of acquisitions N.

At step S103, controller 50 causes prism vibration controller 52 to start vibrating to start vibration of ATR prism 20.

The processing order of steps S100 to S103 above may be changed.

At steps S104 and S105, infrared photodetector 30 detects S(a) and S(b) in synchronization with the vibration of ATR prism 20. At step S104, in the weak adhesion state, controller 50 causes infrared photodetector 30 to detect the intensity of radiated infrared light 11c and output it to controller 50. Controller 50 takes the obtained intensity of radiated infrared light 11c as S(a). At step 105, in the strong adhesion state, controller 50 causes infrared photodetector 30 to detect the intensity of radiated infrared light 11c and output it to controller 50. Controller 50 takes the obtained intensity of radiated infrared light 11 as S(b). Herein, the order of steps S104 and S105 may be changed.

At step S106, controller 50 calculates and stores dS=S(a)−S(b). When ATR prism 20 and measurement skin 40 are brought into contact with each other manually for preparation for measurement before ATR prism 20 is vibrated in order to calculate an amount of sugar in measurement skin 40, it is difficult to keep, for example, a size of a gap between ATR prism 20 and measurement skin 40 constant in each measurement. That is to say, it is difficult to accurately provide the weak adhesion state, which is an initial state, manually. Although S(a) and S(b) accordingly have values varying for each measurement, obtaining a difference between S(a) and S(b) can obtain a value which is not affected by variations for each measurement. That is to say, dS can reflect an amount of sugar in measurement skin 40 with high accuracy.

At step S107, controller 50 compares a number of dS acquisitions n obtained so far with limited number of acquisitions N set at step S103. If number of acquisitions n is smaller than limited number of acquisitions N, the process returns to step S104, and the processes of steps S104 to 107 are repeated. When number of acquisitions n becomes equal to limited number of acquisitions N, the process proceeds to step S108.

At step S108, controller 50 calculates a sum ΣdS of all the stored dS's. Sum ΣdS is obtained in order to smooth a measurement error. Sum ΣdS may be further divided by limited number of acquisitions N to obtain an average ΣdS/N.

At step S109, controller 50 displays the calculated value ΣdS on display 54.

Herein, limited number of acquisitions N at step 103 can be freely determined by a user or a designer. Increasing limited number of acquisitions N can improve signal-noise ratio S/N of ΣdS obtained at step 108, whereas a time required for measurement increases as well.

The present embodiment can detect infrared light radiated from ATR prism 20 in synchronization with the vibration of ATR prism 20, as described above. An amount of a biological material in measurement skin 40 can be measured accurately by obtaining a difference between the intensity of infrared light in the strong adhesion state and the intensity of infrared light in the weak adhesion state between ATR prism 20 and measurement skin 40.

[Notes]

A biological material measuring apparatus (80) and a method of measuring a biological material of Embodiment 1 have the following characteristics.

(1) The biological material measuring apparatus (80) includes an ATR prism (20), an infrared light source (32), an infrared photodetector (30), a prism vibration controller (52), and a controller (50). The ATR prism (20) is adherable to a measurement skin (40). The infrared light source (32) radiates, to the ATR prism (20), infrared light in entirety or part of a wavelength region with absorption wavelengths of a biological material. The infrared photodetector (30) detects infrared light emitted from the ATR prism (20). The prism vibration controller (52) is mounted on the ATR prism (20) and vibrates the ATR prism (20) perpendicular to a contact surface between the ATR prism (20) and the measurement skin (40). The controller (50) causes the infrared photodetector (30) to detect the infrared light in synchronization with the vibration.

Consequently, an amount of a biological material in the measurement skin (40) can be measured accurately.

(2) The prism vibration controller (32) causes the ATR prism (20) to vibrate periodically. The controller (50) causes the infrared photodetector (30) to detect infrared light two or more times during a period of the vibration of the ATR prism (20).

Consequently, high detection sensitivity can be obtained.

(3) The controller (50) causes the infrared photodetector (30) to detect the infrared light at a timing of a weak adhesion state in which the lowest pressure acts on the contact surface between the ATR prism (20) and the measurement skin (40) during the period of the vibration, and detect the infrared light at a timing of a strong adhesion state in which the highest pressure acts on the contact surface between the ATR prism (20) and the measurement skin (40) during the period of the vibration.

Consequently, higher detection sensitivity can be obtained.

(4) The controller (50) calculates a difference between a detection value of the infrared light which is detected at the timing of the weak adhesion state during the period of the vibration and a detection value of the infrared light which is detected at the timing of the strong adhesion state during the period of the vibration.

Consequently, an amount of a biological material can be measured without an effect of variations in the adhesion state between ATR prism (20) and measurement skin (40) for each measurement.

(5) The controller (50) calculates a plurality of the differences over a plurality of the periods and calculates a sum or an average of the plurality of differences calculated.

Consequently, a noise component included in a measurement value can be eliminated.

(6) A method of measuring a biological material includes: by an infrared light source (32), radiating infrared light in entirety or part of a wavelength region with absorption wavelengths of a biological material; by an ATR prism (20), which is in contact with a measurement skin (40), receiving infrared light radiated from the infrared light source (32), causing the infrared light to pass through the ATR prism (20), and then emitting the infrared light to outside; vibrating the ATR prism (20) perpendicular to a contact surface between the ATR prism (20) and the measurement skin (40); by an infrared photodetector (30), detecting the infrared light emitted from the ATR prism (20) at a timing of a weak adhesion state in which the lowest pressure acts on the contact surface between the ATR prism and the measurement skin; by the infrared photodetector (30), detecting the infrared light emitted from the ATR prism (20) at a timing of a strong adhesion state in which the highest pressure acts on the contact surface between the ATR prism (20) and the measurement skin (40) during a period of the vibration; and calculating a difference between a detection value of the infrared light which is detected at the timing of the weak adhesion state during the period of the vibration and a detection value of the infrared light which is detected at the timing of the strong adhesion state during the period of the vibration.

Consequently, an amount of a biological material in the measurement skin (40) can be measured accurately.

Embodiment 2

The configuration of a non-invasive blood sugar level sensor 80 of Embodiment 2 is similar to the configuration of the non-invasive blood sugar level sensor of Embodiment 1 except for the function of controller 50.

Embodiment 2 differs from Embodiment 1 in that the number of detections of radiated infrared light 11c in infrared photodetector 30 during one period of vibration of ATR prism 20 is two or more times. In the present embodiment, infrared photodetector 30 detects the intensity of radiated infrared light 11c eight times at equal intervals during one period of vibration of ATR prism 20.

Assume that the amplitude of vibration of ATR prism 20 is d, the period of vibration is T, and the number of sampling during one period is eight times. Although the number of sampling may be less than eight times for rougher measurements and may be more than eight times for finer measurements, the sampling interval is equal in any case.

Figure 6:
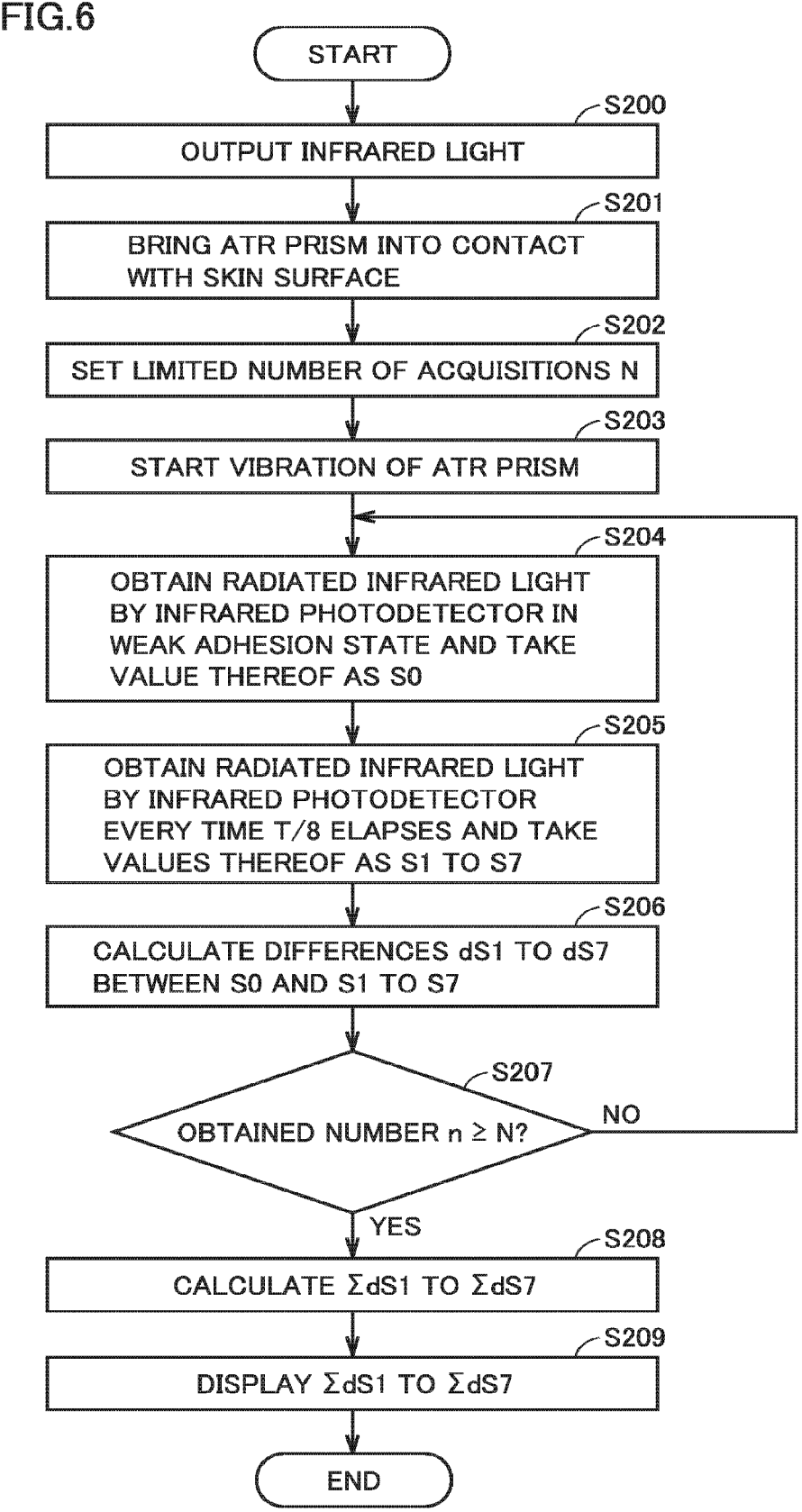
FIG. 6 is a flowchart showing an operational procedure of mobile non-invasive blood sugar level sensor 80 of Embodiment 2.

FIG. 6 is a flowchart showing an operational procedure of mobile non-invasive blood sugar level sensor 80 in Embodiment 2.

Steps S200 to S203 are similar to steps S100 to S103 of Embodiment 1, description of which will not be repeated.

At steps S204 and S205, infrared photodetector 30 detects S0 to S7 in synchronization with the vibration. At step S204, in the weak adhesion state, controller 50 causes infrared photodetector 30 to detect the intensity of radiated infrared light 11c and output it to controller 50. Controller 50 takes the obtained intensity of radiated infrared light 11c as S0. Although a timing at which a measurement is started may be the weak adhesion state or the strong adhesion state, the weak adhesion state is a start timing in FIG. 6.

At step S205, controller 50 causes infrared photodetector 30 to detect radiated infrared light 11c every time a T/8 period elapses from step S204 and output it to controller 50. Controller 50 takes the intensities of radiated infrared light 11c sequentially obtained as S1, S2, S3, S4, S5, S6, and S7.

At step S206, controller 50 calculates and stores differences dS1 (=S0−S1), dS2 (=S0−S2), dS3 (=S0−S3), dS4 (=S0−S4), dS5 (=S0−S5), dS6 (=S0−S6), and dS7 (=S0−S7) between S0 obtained at step S204 and values S1 to S7 obtained at step S205. dS1 to dS7 are determined as described above to obtain the distribution of sugar for each depth from skin surface 60 in measurement skin 40. For example, a difference between dS2 and dS1 is a value indicating a difference between the amount of sugar at a depth of skin surface 60, which corresponds to a penetration length of evanescent light from the timing of the weak adhesion state to a timing T/8, and the amount of sugar at a depth of skin surface 60, which corresponds to a penetration length of evanescent light from the timing of the weak adhesion state to a timing 2T/8.

At step S207, controller 50 compares a number of acquisitions n of each dSi (i to 7) obtained so far and limited number of acquisitions N set at step S203. If number of acquisitions n is smaller than limited number of acquisitions N, the process returns to step S204, and the processes of steps S204 to 207 are repeated. When number of acquisitions n becomes equal to limited number of acquisitions N, the process proceeds to step S208.

At step S208, controller 50 calculates sums ΣdS1, ΣdS2, ΣdS3, ΣdS4, ΣdS5, ΣdS6, and ΣdS7 of all the stored dS1's, dS2's, dS3's, dS4's, dS5's, dS6's, and dS7's, respectively. For example, ΣdS1 is a sum of dS1's in N-times measurements. Sum ΣdS is obtained in order to smooth a measurement error. Sums ΣdS1 to ΣdS7 may be further divided by limited number of acquisitions N to obtain averages ΣdS1/N to ΣdS7/N.

At step S209, controller 50 displays the calculated values ΣdS1, ΣdS2, ΣdS3, ΣdS4, ΣdS5, ΣdS6, and ΣdS7 on display 54.

Figure 7:
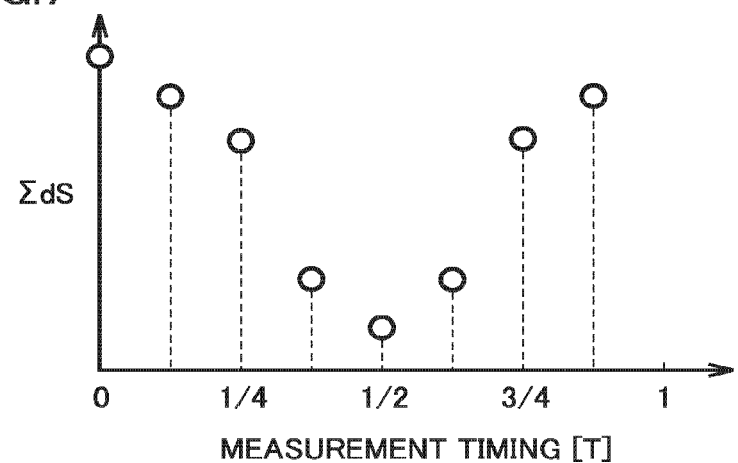
FIG. 7 shows examples of a measurement timing k×T/8 and ΣdSk.

FIG. 7 shows examples of measurement timing k×T/8 and ΣdSk.

In FIG. 7, the horizontal axis represents a measurement timing, that is, a timing at which radiated infrared light 11c is detected by infrared photodetector 30 when ATR prism 20 is vibrated in a period T; the vertical axis represents sum ΣdSk at each timing k T/8.

Since a vibration amplitude d of ATR prism 20 is obtained in advance, controller 50 can convert the measurement timing of FIG. 7 into a press distance by which ATR prism 20 is pressed perpendicularly against measurement skin 40. It is converted into a perpendicular distance of measurement skin 40. That is to say, measurement timings 0, T/8, 2T/8, 3T/8, 4T/8, 5T/8, 6T/8, and 7T/8 are converted respectively into press distances 0, d/4, d/2, 3d/4, d, 3d/4, d/2, and d/4 by which ATR prism 20 is pressed perpendicularly against measurement skin 40.

Figure 8:
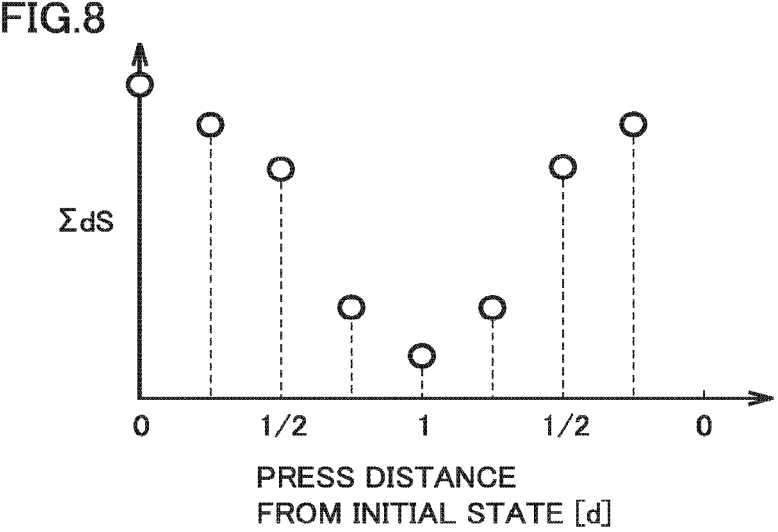
FIG. 8 is similar to FIG. 7, where the measurement timing of the horizontal axis of FIG. 7 is changed to a press distance by which an ATR prism 20 is pressed against a skin surface 60.

FIG. 8 is similar to FIG. 7, where the measurement timing represented by the horizontal axis of FIG. 7 is changed to a press distance by which ATR prism 20 is pressed perpendicularly against measurement skin 40.

As shown in FIGS. 7 and 8, the value of ΣdSk takes the minimum value at measurement timing T/2 and press distance d, and then, returns to its original value.

Embodiment 2 can obtain information regarding the distribution of sugar for each depth from the skin surface, as described above.

[Notes]

A biological material measuring apparatus (80) and a method of measuring a biological material of Embodiment 2 have the following characteristics.

(1) The controller (50) causes the infrared photodetector (30) to detect infrared light at three or more timings during the period of the vibration of the ATR prism (20).

Consequently, the distribution of a biological material perpendicular to the surface of the measurement skin (40) can be measured.

(2) The controller (50) causes the infrared photodetector (30) to detect the infrared light at a timing of a weak adhesion state in which the lowest pressure acts on the contact surface between the ATR prism (20) and the measurement skin (40) during the period of the vibration, and calculates, as a difference at each timing, a difference between a detection value of the infrared light which is detected at the timing of the weak adhesion state during the period of the vibration and a detection value of the infrared light which is detected at each timing of the three or more timings during the period of the vibration other than the timing of the weak adhesion state.

Consequently, the distribution of a biological material perpendicular to the surface of the measurement skin (40) can be measured finely.

(3) The controller (50) calculates a plurality of differences at each timing over a plurality of the periods and calculates a sum or an average of the plurality of the differences calculated at each timing.

Consequently, a noise component included in a measurement value can be eliminated.

(4) The controller (50) converts a detection timing at which the infrared light is detected into a press distance by which the ATR prism (20) is pressed perpendicularly against the measurement skin (40).

Consequently, an amount of a biological material per multiple distances perpendicular to the surface of the measurement skin (40) can be measured.

(5) The controller (50) causes the infrared photodetector (30) to detect the infrared light at equal time intervals during the period.

Consequently, an amount of a biological material present for each certain interval perpendicular to the surface of the measurement skin (40) can be measured.

(6) The method of measuring a biological material includes: by an infrared light source (32), radiating infrared light in entirety or part of a wavelength region with absorption wavelengths of a biological material; by an ATR prism (20), which is in contact with a measurement skin (40), receiving the infrared light radiated from the infrared light source (32), causing the infrared light to pass through the ATR prism (20) while repeating reflection, and then emitting the infrared light to outside; vibrating the ATR prism (20) perpendicular to a contact surface between the ATR prism (20) and the measurement skin (40); by an infrared photodetector (30), detecting the infrared light emitted from the ATR prism (20) at a timing of a weak adhesion state in which the lowest pressure acts on the contact surface between the ATR prism (20) and the measurement skin (40) during a period of the vibration; by the infrared photodetector (30), detecting the infrared light emitted from the ATR prism (20) at two or more timings during the period of the vibration other than the timing of the weak adhesion state; and calculating a difference between a detection value of the infrared light which is detected at the timing of the weak adhesion state during the period of the vibration and a detection value of the infrared light which is detected at each timing of the two or more timings other than the timing of the weak adhesion state.

Consequently, the distribution of a biological material perpendicular to the surface of the measurement skin (40) can be measured.

Embodiment 3

Figure 9:
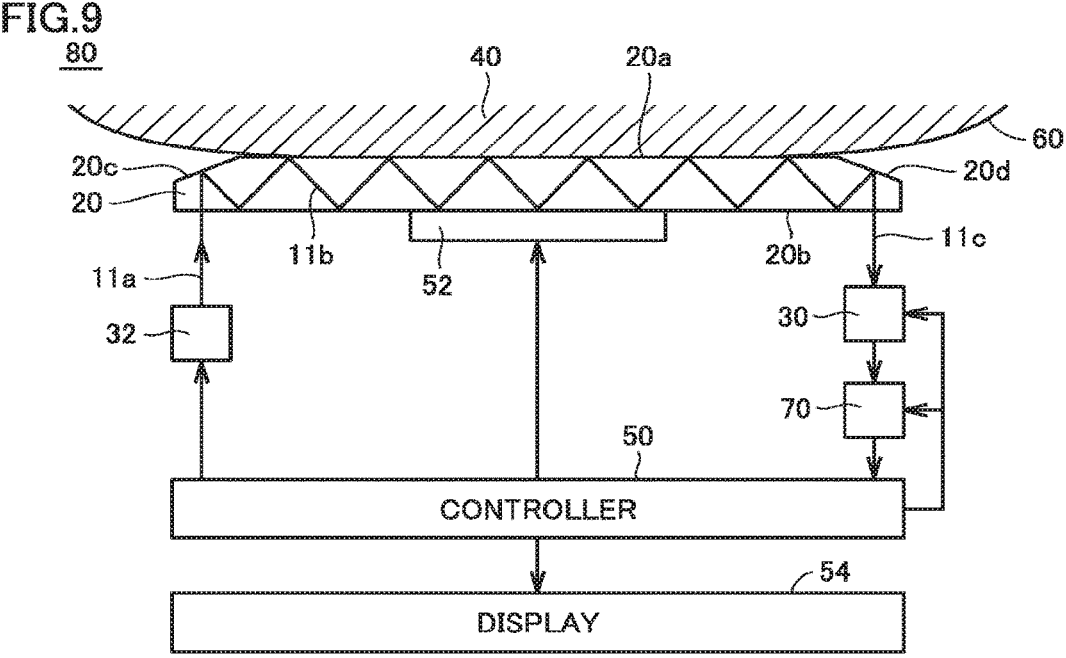
FIG. 9 shows a configuration of mobile non-invasive blood sugar level sensor 80 of Embodiment 3.

FIG. 9 shows a configuration of a mobile non-invasive blood sugar level sensor 80 of Embodiment 3.

As shown in FIG. 9, blood sugar level sensor 80 includes infrared light source 32, ATR prism 20, infrared photodetector 30, prism vibration controller 52, controller 50, and a lock-in amplifier 70.

The configuration of blood sugar level sensor 80 of Embodiment 3 differs from the configuration of blood sugar level sensor 80 of Embodiment 1 or 2 in that blood sugar level sensor 80 of Embodiment 3 includes lock-in amplifier 70.

A measurement signal indicating the intensity of radiated infrared light 11c which is detected by infrared photodetector 30 is input to lock-in amplifier 70. This measurement signal is a feeble signal. In detection of a feeble signal, noise needs to be eliminated because noise greatly affects the detection. An example way of eliminating noise uses a band-pass filter. When the device used for the band-pass filter fluctuates, a center frequency fluctuates, which affects the amplitude of a signal. The band-pass filter is thus unstable for detection of a feeble signal.

The present embodiment uses a frequency conversion technique by lock-in amplifier 70 in order to detect a measurement signal, which is a feeble signal buried in noise. The frequency conversion technique uses a phase sensitive detector (PSD) to extract a target feeble signal from among the signals buried in noise. Since a signal obtained by eliminating noise of lock-in amplifier 70 is a direct current, the filer whose bandwidth is limited may require a low-pass filter alone. In the low-pass filter, the cut-off frequency merely fluctuates even when a device used fluctuates, which does not affect the value of a DC signal.

Figure 10:
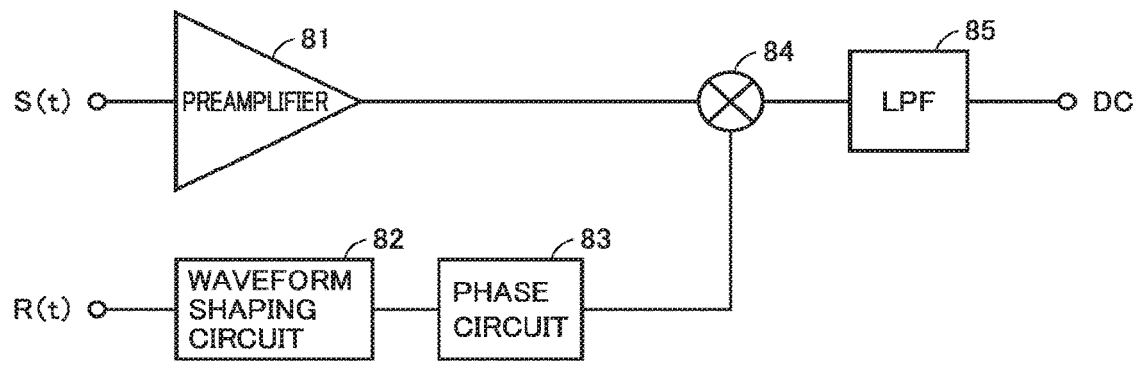
FIG. 10 shows a configuration of a lock-in amplifier 70.

FIG. 10 shows a configuration of lock-in amplifier 70.

Lock-in amplifier 70 includes a preamplifier 81, a waveform shaping circuit 82, a phase circuit 83, a PSD 84, and a low-pass filter (LPF) 85.

Lock-in amplifier 70 receives an input of a measurement signal S(t) indicating the intensity of radiated infrared light 11c, which is expressed by $S(t)=A \sin(\omega t+a)$ wherein the frequency of ATR prism 20 is f, where $\omega=2\pi f$. Lock-in amplifier 70 also receives an input of a reference signal R(t), which is expressed by $R(t)=A \sin(\sigma t+b)$.

Preamplifier 81 amplifies measurement signal S(t) to a desired voltage.

Waveform shaping circuit 82 shapes reference signal R(t) into a rectangular wave. Phase circuit 83 adjusts a phase difference between a reference signal R'(t) of a rectangular wave and measurement signal S(t). Specifically, phase circuit 83 adjusts a phase difference (a-b) between reference signal R'(t) and measurement signal S(t) to "0".

PSD 84 multiplies the signal waveforms of measurement signal S(t) and reference signal R'(t) together. Making an adjustment such that a=b allows PSD 84 to obtain a maximum DC component $A/2\times\cos(b-a)(=A/2)$ and an AC component $A/2\times\cos(2\omega t+a+b)(=A/2\times\cos(2\omega t+2a))$ of a double frequency.

LPF 85 removes an AC component from a signal output from PSD 84 and extracts a DC component, thus outputting a DC component of measurement signal S(t). Consequently, only a target signal buried in noise can be extracted as the maximum value of the DC component.

Figure 11:
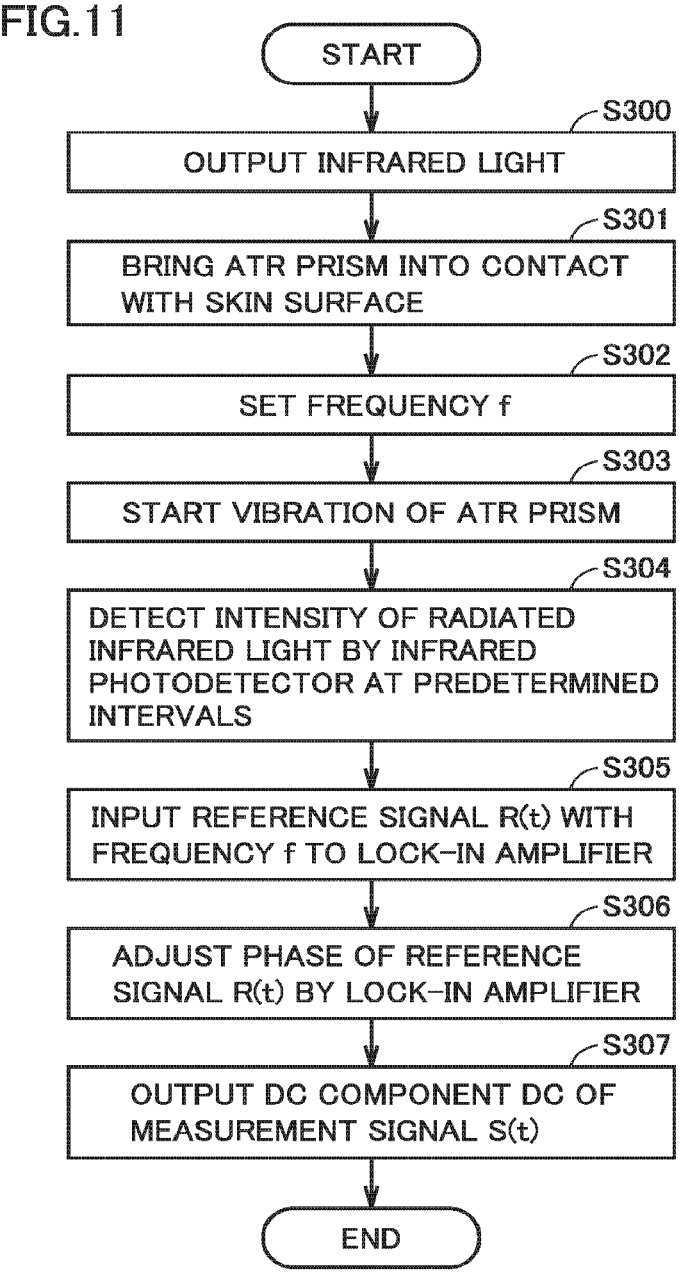
FIG. 11 is a flowchart showing an operational procedure of non-invasive blood sugar level sensor 80 of Embodiment 3.

FIG. 11 is a flowchart showing an operational procedure of blood sugar level sensor 80 in Embodiment 3.

Although the infrared light emitted from the infrared light source repeats reflection within the ATR prism and enters the infrared photodetector, a signal detected by the infrared photodetector may be a feeble signal, and accordingly, a signal with a high signal-noise ratio SN needs to be obtained.

At step S300, infrared light source 32 outputs infrared light.

At step S301, ATR prism 20 is brought into contact with skin surface 60 of the subject.

At step S302, controller 50 sets a frequency f of a displacement of ATR prism 20.

At step S303, controller 50 causes prism vibration controller 52 to start vibration at frequency f to start vibration of ATR prism 20 at frequency f of the displacement.

At this time, it suffices that the vibration of ATR prism 20 has a movement width by which ATR prism 20 does not move away from skin surface 60 of the subject that is a measurement target in the upward and downward movements of vibration, which may be, for example, a movement of going back and forth between the weak adhesion state of FIG. 2 and the strong adhesion state of FIG. 3.

At step S304, controller 50 causes infrared photodetector 30 to detect the intensity of radiated infrared light 11c at predetermined intervals and output it to controller 50. Controller 50 generates a measurement signal S(t) indicating the obtained intensity of the radiated infrared light 11.

At step S305, controller 50 outputs a reference signal R(t)=A sin(ωt+b) with frequency f to lock-in amplifier 70.

At step S306, preamplifier 81 of lock-in amplifier 70 amplifies a measurement signal S(t) indicating the intensity of radiated infrared light 11c output at predetermined intervals from infrared photodetector 30 to a desired voltage. Waveform shaping circuit 82 of lock-in amplifier 70 shapes reference signal R(t) into a rectangular wave. Phase circuit 83 of lock-in amplifier 70 adjusts a phase difference between reference signal R'(t) of a rectangular wave and measurement signal S(t) to "0". PSD 84 of lock-in amplifier 70 multiplies the signal waveforms of measurement signal S(t) and reference signal R'(t) together. Adjusting a phase difference to "0" by phase circuit 83 allows PSD 84 to output a maximum DC component and an AC component of a double frequency.

At step S307, LPF 85 of lock-in amplifier 70 removes an AC component from the signal output from PSD 84 and extracts a DC component, thus outputting a DC component of measurement signal S(t). When measurement signal S(t) is expressed by A sin(ωt+a), A/2 is output.

As described above, the present embodiment can obtain a maximum DC value of a target signal to increase measurement accuracy.

[Notes]

A biological material measuring apparatus (80) of Embodiment 3 has the following characteristics.

(1) The biological material measuring apparatus (80) further includes a lock-in amplifier (70) configured to receive an input of a signal output from the infrared photodetector (30).

Consequently, a signal output from the infrared photodetector (30) can be detected even when the signal has such a feeble magnitude as to be buried in noise.

(2) The controller (50) controls the prism vibration controller (52) such that the ATR prism (20) vibrates at a frequency equal to a frequency of a reference signal input to the lock-in amplifier (70).

Consequently, the lock-in amplifier (70) can output a maximum DC value of the signal output from the infrared photodetector (30) to increase measurement accuracy.

Embodiment 4

As described in the above embodiments, evanescent light is generated at an interface at which reflection occurs, and the evanescent light penetrates a measurement skin. Since the evanescent light is absorbed and scattered by water, sugar, and any other biological material at that time, the intensity of the infrared light propagating through ATR prism 20 attenuates. A penetration length dp of this evanescent light is represented by expression below:

[Math 1]

$$dp = \frac{\lambda}{2\pi n1}[\sin^2\theta - (n2/n1)^2]^{-1/2} \quad (1)$$

where n1 is an index of refraction of a prism, n2 is an index of refraction of a measurement object, θ is an angle of incidence, and λ is a wavelength to be used.

Figure 12:
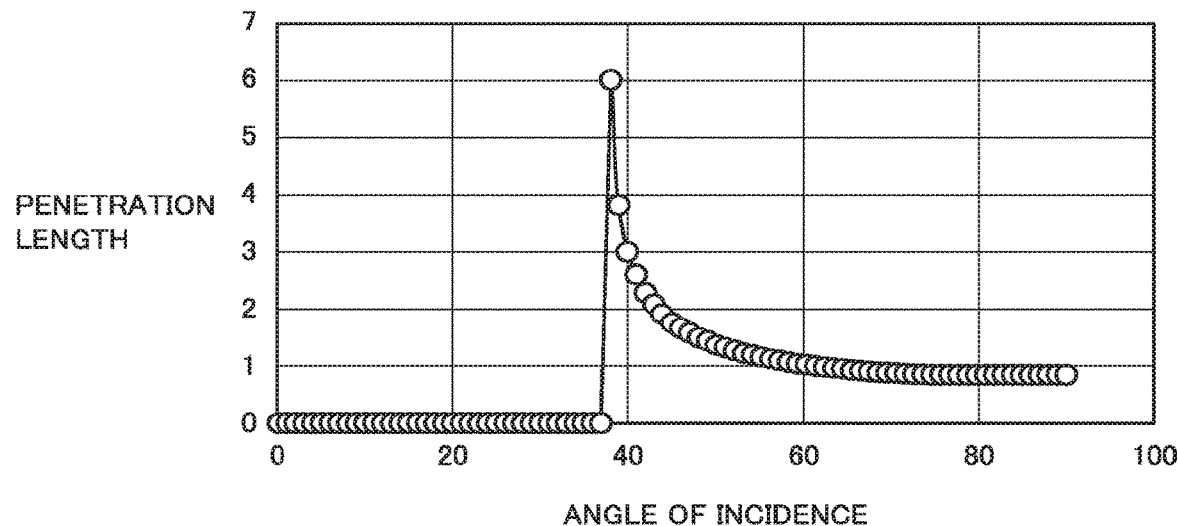
FIG. 12 shows an example penetration length of evanescent light relative to an angle of incidence of infrared light at indices of refraction n1 and n2.

FIG. 12 shows an example of the penetration length of evanescent light relative to the angle of incidence of infrared light at indices of refraction n1 and n2.

As shown in FIG. 12, the penetration length of evanescent light reaches its maximum value at an angle of incidence of 40°. Slightly changing an angle of incidence greatly changes the penetration length of evanescent light.

Figure 13:
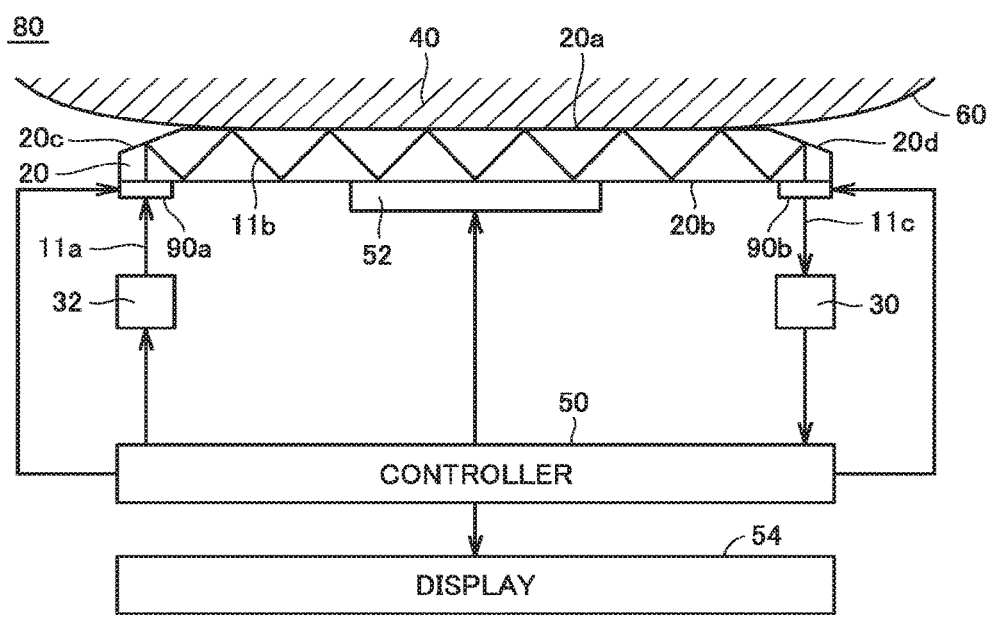
FIG. 13 shows a configuration of mobile non-invasive blood sugar level sensor 80 of Embodiment 4.

FIG. 13 shows a configuration of mobile non-invasive blood sugar level sensor 80 of Embodiment 4. Blood sugar level sensor 80 of FIG. 13 differs from blood sugar level sensor 80 of Embodiment 1 shown in FIG. 2 in that blood sugar level sensor 80 of FIG. 13 includes angle adjusting devices 90a and 90b.

Angle adjusting device 90a is provided between infrared light source 32 and ATR prism 20. Angle adjusting device 90a is formed of a mirror or a lens. Angle adjusting device 90a adjusts the angle of incidence of infrared light with respect to ATR prism 20.

Angle adjusting device 90b is provided between ATR prism 20 and infrared photodetector 30. Angle adjusting device 90b is formed of a mirror or a lens. Angle adjusting device 90b adjusts the travel direction of infrared light such that the infrared light emitted from ATR prism 20 travels toward infrared photodetector 30.

When the angle of incidence of the infrared light with respect to ATR prism 20 at which the penetration length of the evanescent light reaches its maximum value is 00, angle adjusting device 90a periodically changes the angle of incidence around 00 in a range in which a penetration length can be secured. Consequently, the angle of incidence with respect to ATR prism 20 oscillates in a certain range, and the penetration length of the evanescent light changes periodically from large length to small length to large length. Angle adjusting device 90b adjusts the angle of the light emitted from ATR prism 20 in synchronization with angle adjusting device 90a.

The angle of end face 20d of ATR prism 20 is set to allow radiated infrared light 11c to perpendicularly enter infrared photodetector 30 in the absence of angle adjusting device 90a. Although the adjustment of the angle of incidence of the infrared light by angle adjusting device 90a changes the angle of emission of the infrared light emitted from ATR prism 20, angle adjusting device 90b can adjust the travel direction of the infrared light emitted from ATR prism 20 to allow radiated infrared light 11c to perpendicularly enter infrared photodetector 30. How much angle is to be adjusted by angle adjusting device 90b relative to the amount of angle of incidence which is adjusted by angle adjusting device 90a can be determined in advance.

In the example of FIG. 12, angle adjusting device 90a periodically adjusts the angle of the infrared light which is incident on ATR prism 20 such that the angle of incidence of the infrared light with respect to ATR prism 20 periodically changes from 38° to 41° to 38°. Angle adjusting device 90b periodically adjusts the travel direction of the infrared light emitted from ATR prism 20 in synchronization with angle adjusting device 90a such that the infrared light emitted from ATR prism 20 perpendicularly enters infrared photodetector 30.

The periods in which the angles are adjusted by angle adjusting device 90a and angle adjusting device 90b coincide with the periods in which prism vibration controller 52 vibrates in Embodiment 1.

In Embodiment 1, prism vibration controller 52 repeats the strong adhesion state and the weak adhesion state. In the present embodiment, angle adjusting device 90a adjusts the angle of incidence of infrared light with respect to ATR prism 20 such that the angle of incidence of infrared light with respect to ATR prism 20 reaches its maximum in the weak adhesion state during one period of vibration and that the angle of incidence of infrared light with respect to ATR prism 20 reaches its minimum in the strong adhesion state during one period of vibration. Consequently, evanescent light penetrates a measurement object more deeply in the strong adhesion state, and evanescent light penetrates a measurement object more shallowly in the weak adhesion state.

In the present embodiment, as described above, the angle of incidence of the infrared light with respect to ATR prism 20 can be changed to determine the intensity of infrared light in the strong adhesion state and the intensity of infrared light in the weak adhesion state, as in the method of vibrating ATR prism 20 in Embodiment 1. Consequently, the present embodiment can also measure the amount of a biological material in measurement skin 40 accurately as in Embodiment 1.

[Notes]

A biological material measuring apparatus (80) of Embodiment 4 has the following characteristics.

(1) The biological material measuring apparatus (80) includes a first angle adjusting device (90a) and a second angle adjusting device (90b). The first angle adjusting device (90a) is provided between the infrared light source (32) and the ATR prism (20) for adjusting an angle of incidence of the infrared light with respect to the ATR prism (20). The second angle adjusting device (90b) is provided between the ATR prism (20) and the infrared photodetector (32) for adjusting a travel direction of the infrared light emitted from the ATR prism (20).

Consequently, the amount of a biological material in the measurement skin (40) can be measured accurately.

(2) The biological material measuring apparatus (80) includes an angle adjusting device (90a) provided between the infrared light source (32) and the ATR prism (20). The angle adjusting device (90a) adjusts an angle of incidence of the infrared light with respect to the ATR prism (20) such that an angle of incidence of the infrared light with respect to the ATR prism (20) reaches its maximum in the weak adhesion state during one period of vibration and that an angle of incidence of the infrared light with respect to the ATR prism (20) reaches its minimum in the strong adhesion state during one period of vibration.

Consequently, higher detection sensitivity can be obtained.

Embodiment 5

Figure 14:
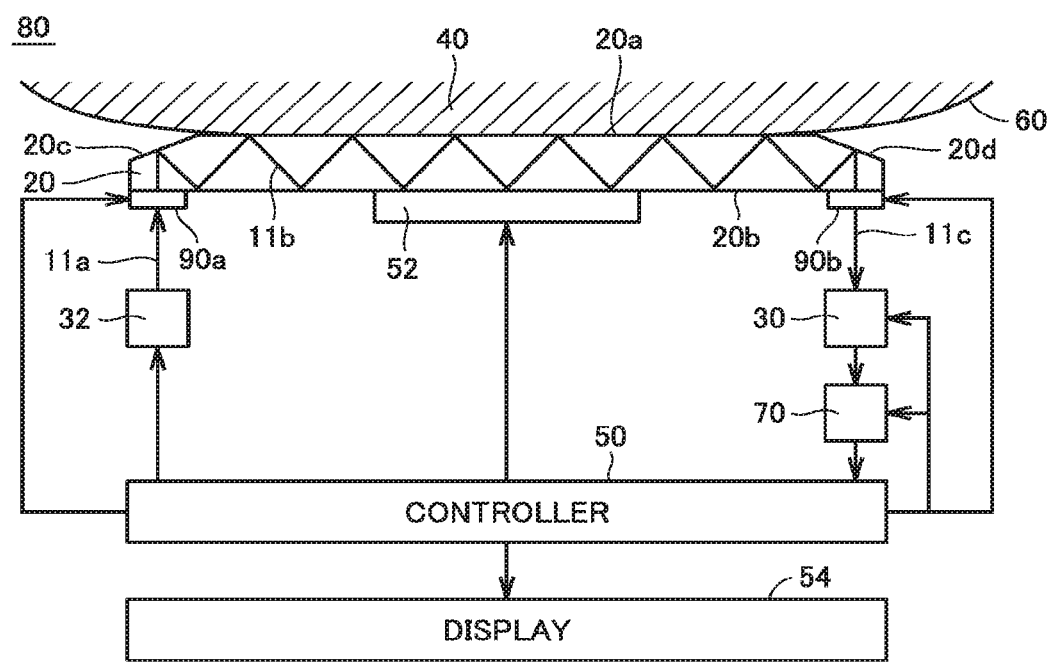
FIG. 14 shows a configuration of mobile non-invasive blood sugar level sensor 80 of Embodiment 5.

FIG. 14 shows a configuration of a mobile non-invasive blood sugar level sensor 80 of Embodiment 5. Blood sugar level sensor 80 of FIG. 14 differs from blood sugar level sensor 80 of Embodiment 3 shown in FIG. 9 in that blood sugar level sensor 80 of FIG. 14 includes angle adjusting devices 90a and 90b.

Angle adjusting device 90a and angle adjusting device 90b are disposed and operate as described in Embodiment 4.

It is to be understood that the embodiments disclosed herein are presented for the purpose of illustration and non-restrictive in every respect. It is therefore intended that the scope of the present invention is defined by claims, not only by the embodiments described above, and encompasses all modifications and variations equivalent in meaning and scope to the claims.

REFERENCE SIGNS LIST 11a incoming infrared light, 11b propagating infrared light, 11c radiated infrared light, 20 ATR prism, 20a, 20b, 20c, 20d ATR prism end face, 30 infrared photodetector, 32 infrared light source, 40 measurement skin, 50 controller, 52 prism vibration controller, 54 display, 60 skin surface, 80 blood sugar level sensor, 81 preamplifier, 82 waveform shaping circuit, 83 phase circuit, 84 PSD, 85 LPF, 90a, 90b angle adjusting device.

The invention claimed is:

1. A biological material measuring apparatus comprising:
   an attenuated total reflection (ATR) prism adherahle to a measurement skin;
   an infrared light source configured to radiate, to the ATR prism, infrared light in entirety or part of a wavelength region with absorption wavelengths of a biological material;
   an infrared photodetector configured to detect infrared light emitted from the ATR prism;
   a prism vibration controller mounted on the ATR prism and configured to vibrate the ATR prism perpendicular to a contact surface between the ATR prism and the measurement skin; and
   a controller configured to cause the infrared photodetector to detect the infrared light in synchronization with the vibration.

2. The biological material measuring apparatus according to claim 1, wherein
   the prism vibration controller is configured to cause the ATR prism to vibrate periodically, and
   the controller is configured to cause the infrared photodetector to detect infrared light two or more times during a period of the vibration of the ATR prism.

3. The biological material measuring apparatus according to claim 2, wherein the controller is configured to cause the infrared photodetector to
   detect the infrared light at a timing of a weak adhesion state in which a lowest pressure acts on the contact surface between the ATR prism and the measurement skin during the period of the vibration, and
   detect the infrared light at a timing of a strong adhesion state in which a highest pressure acts on the contact surface between the ATR prism and the measurement skin during the period of the vibration.

4. The biological material measuring apparatus according to claim 3, wherein the controller is configured to calculate a difference between a detection value of the infrared light which is detected at the timing of the weak adhesion state during the period of the vibration and a detection value of the infrared light which is detected at the timing of the strong adhesion state during period of the vibration.

5. The biological material measuring apparatus according to claim 4, wherein the controller is configured to calculate a plurality of the differences over a plurality of the periods and calculate a sum or an average of the plurality of differences calculated.

6. The biological material measuring apparatus according to claim 3, comprising an angle adjusting device provided between the infrared light source and the ATR prism,
wherein the angle adjusting device is configured to adjust an angle of incidence of the infrared light with respect to the ATR prism such that
the angle of incidence of the infrared light with respect to the AIR prism reaches its maximum in the weak adhesion state during the period of the vibration, and
the angle of incidence of the infrared light with respect to the ATR prism reaches its minimum in the strong adhesion state during the period of the vibration.

7. The biological material measuring apparatus according to claim 2, wherein the controller is configured to cause the infrared photodetector to detect the infrared light at three or more timings during the period of the vibration of the AIR prism.

8. The biological material measuring apparatus according to claim 7, wherein the controller is configured to
cause the infrared photodetector to detect the infrared light at a timing of a weak adhesion state in which a lowest pressure acts on the contact surface between the ATR prism and the measurement skin during the period of the vibration, and
calculate, as a difference at each timing, a difference between a detection value of the infrared light which is detected at the timing of the weak adhesion state during the period of the vibration and a detection value of the infrared light which is detected at each timing of the three or more timings during the period of the vibration other than the timing of the weak adhesion state.

9. The biological material measuring apparatus according to claim 8, wherein the controller is configured to calculate a plurality of the differences at each timing over a plurality of the periods and calculate a sum or an average of the plurality of differences calculated at each timing.

10. The biological material measuring apparatus according to claim 9, wherein the controller is configured to convert a detection timing at which the infrared light is detected into a press distance by which the ATR prism is pressed perpendicularly against the measurement skin.

11. The biological material measuring apparatus according to claim 8, wherein the controller is configured to convert a detection timing at which the infrared light is detected into a press distance by which the ATR prism is pressed perpendicularly against the measurement skin.

12. The biological material measuring apparatus according to claim 7, wherein the controller is configured to cause the infrared photodetector to detect the infrared light at equal time intervals during the period.

13. The biological material measuring apparatus according to claim 1, further comprising a lock-in amplifier configured to receive an input of a signal output from the infrared photodetector.

14. The biological material measuring apparatus according to claim 13, wherein the controller is configured to control the prism vibration controller such that the ATR prism vibrates at a frequency equal to a frequency of a reference signal input to the lock-in amplifier.

15. The biological material measuring apparatus according to claim 1, comprising:
a first angle adjusting device provided between the infrared light source and the AIR prism for adjusting an angle of incidence of the infrared light with respect to the ATR prism; and
a second angle adjusting device provided between the AIR prism and the infrared photodetector for adjusting a travel direction of the infrared light emitted from the ATR prism.

16. A method of measuring a biological material, the method comprising:
by an infrared light source, radiating infrared light in entirety or part of a wavelength region with absorption wavelengths of a biological material;
by an attenuated total reflection (ATR) prism, which is in contact with a measurement skin, receiving the infrared light radiated from the infrared light source, causing the infrared light to pass through the ATR prism, and then emitting the infrared light to outside;
vibrating the ATR prism perpendicular to a contact surface between the ATR prism and the measurement skin;
by an infrared photodetector, detecting the infrared light emitted from the ATR prism at a timing of a weak adhesion state in which a lowest pressure acts on the contact surface between the ATR prism and the measurement skin during a period of the vibration;
by the infrared photodetector, detecting the infrared light emitted from the ATR prism at a timing of a strong adhesion state in which a highest pressure acts on the contact surface between the ATR prism and the measurement skin during the period of the vibration; and
calculating a difference between a detection value of the infrared light which is detected at the timing of the weak adhesion state during the period of the vibration and a detection value of the infrared light which is detected at the timing of the strong adhesion state during the period of the vibration.

17. A method of measuring a biological material, the method comprising:
by an infrared light source, radiating infrared light in entirety or part of a wavelength region with absorption wavelengths of a biological material;
by an attenuated total reflection (ATR) prism, which is in contact with a measurement skin, receiving the infrared light radiated from the infrared light source, causing the infrared light to pass through the ATR prism while repeating reflection, and then emitting the infrared light to outside;
vibrating the ATR prism perpendicular to a contact surface between the ATR prism and the measurement skin;
by an infrared photodetector, detecting the infrared light emitted from the ATR prism at a timing of a weak adhesion state in which a lowest pressure acts on the contact surface between the ATR prism and the measurement skin during a period of the vibration;
by the infrared photodetector, detecting the infrared light emitted from the ATR prism at two or more timings during the period of the vibration other than the timing of the weak adhesion state; and calculating a difference between a detection value of the infrared light which is detected at the timing of the weak adhesion state during the period of the vibration and a detection value of the infrared light which is detected at each timing of the two or more timings other than the timing of the weak adhesion state.

* * * * *